United States Patent [19]

Mizusawa et al.

[11] Patent Number: 5,338,358
[45] Date of Patent: Aug. 16, 1994

[54] APPARATUS FOR DYEING TISSUES

[75] Inventors: Yoshitada Mizusawa, Nagano; Matsumi Toya, Koushoku, both of Japan

[73] Assignees: Kabushiki Kaisha Tiyoda Seisakusho, Nagano; Sakura Finetechnical Co., Ltd., Tokyo, both of Japan

[21] Appl. No.: 947,512

[22] Filed: Sep. 17, 1992

[30] Foreign Application Priority Data

Apr. 6, 1992 [JP] Japan .................................. 4-112340

[51] Int. Cl.[5] .............................................. B05C 3/00
[52] U.S. Cl. .................... 118/401; 118/429; 422/99
[58] Field of Search ................... 118/401, 429; 422/99, 422/100, 101, 102

[56] References Cited

U.S. PATENT DOCUMENTS

| | | | |
|---|---|---|---|
| 3,892,197 | 7/1975 | Kinney et al. | 118/429 X |
| 4,985,206 | 1/1991 | Bowman et al. | 422/99 |
| 5,068,091 | 11/1991 | Toya | 422/99 |
| 5,080,869 | 1/1992 | McCormick | 422/102 |

FOREIGN PATENT DOCUMENTS 3-111035  5/1991  Japan .
2216261  10/1989  United Kingdom .

*Primary Examiner*—David A. Simmons
*Assistant Examiner*—J. Sells
*Attorney, Agent, or Firm*—Ladas & Parry

[57] ABSTRACT

Apparatus for dyeing tissues sampled from a living body for the purpose of observing immunoreaction of the tissues has a dyeing tray with a plurality of plateaus arranged in parallel disposition. A slide is so placed over each plateau that a wedge-shaped gap of capillary dimension is formed between the plateau and the undersurface of the slide to which a sampled tissue is attached. A liquid drip surface and a liquid discharge port are formed at one end of the top surface of each plateau. A liquid delivery port is formed on a side wall of the tray so as to communicate with the liquid discharge port. The liquid delivery port and the drip surface are always exposed. A dyeing liquid or a rinsing liquid is dripped onto the exposed drip surface and spreads into the gap for dyeing the tissue or rinse the relevant parts. After the dyeing or rinsing, the used liquid is sucked and discharged by way of the liquid delivery port. Because of the exposure of the drip surface and the liquid delivery port, the operation is easy and the dyeing tray can also be used for manual dyeing. A bank between the liquid discharge port and the drip surface prevents direct flow of the liquid therebetween.

11 Claims, 12 Drawing Sheets

APPARATUS FOR DYEING TISSUES

BACKGROUND OF THE INVENTION

1. Field of the Invention

The present invention relates generally to an apparatus for dyeing tissues sampled from a living body for the purpose of observing immunoreaction of the tissues, e.g., in the case where an examination for cancer is performed in hospitals.

2. Description of the Related Arts

In order to diagnose diseases such as cancer, commonly utilized are immunoreaction such an antigen antibody reaction. For the diagnosis of diseases making use of such immunoreaction, pieces of tissue sampled from a living body are attached to glass slides and brought into contact with predetermined dyeing liquids in turn to dye the pieces of tissue.

Conventionally, when performing a dyeing treatment with the aim of observing the immunoreaction, dyeing solutions or liquids are prepared in beaker-like containers, and glass slides to which pieces of tissue are respectively attached are immersed in the dyeing liquid in these containers, thereby bringing the pieces of tissue into contact with the dyeing liquids. This inevitably results in an increase in the volume of the dyeing liquids used. Since most of the dyeing liquids used for the observation of the immunoreaction are expensive, the increase of the amount of the dyeing liquid used is not desirable.

Conventionally, the dyeing operation of the tissues is often manually performed to reduce the treating cost, which is however a time-consuming work and sometimes requires an all-night operation. This is not desirable in terms of the working condition of the workers.

In order to overcome these problems, there has been proposed a tissue dyeing apparatus capable of carrying out an operation of dyeing tissues with a small amount of dyeing liquids (U.S. Pat. No. 5,068,092 to Toya, issued Nov. 26, 1991).

The tissue dyeing apparatus disclosed in this U.S. patent comprises a dyeing block on which a row of rectangular plateaus are formed. The plateaus have flat upper surfaces, respectively. On both sides of the row of plateaus are provided raised supporting surfaces for supporting thereon glass slides in such a manner that the slides are positioned above the plateaus with wedge-shaped capillary gaps formed between the upper surfaces of the plateaus and the undersurfaces of the slides, respectively. Each plateaus has a width greater than the width of the associated slide so that the upper surface of each plateau is exposed on both sides of the associated slide.

A dyeing liquid is dripped from above onto the exposed portion of the upper surface of each plateau. The thus dripped dyeing liquid spreads into the wedge-shaped gap under the slide by virtue of the capillarity and acts on the piece of tissue attached to the undersurface of the slide to dye the piece. After the dyeing operation, the used dyeing liquid is sucked through a liquid discharge port formed on the upper surface of the plateau and is sent to a waste liquid tank.

Thereafter, a cleaning liquid is supplied into the wedge-shaped gap through a cleaning liquid supply port formed on the upper surface of the plateau, for cleaning or rinsing to remove the remaining dyeing liquid. After that, another dyeing liquid is supplied into the gap in the same way as stated above and the same operation as above is repeated.

In the known tissue dyeing apparatus described above, each plateau must be larger in width than the slide to provide a dyeing liquid dripping surface on the plateau, so that the plateaus occupy a relatively large space and the dyeing block becomes bulky for the number of slides that can be accommodated on the dyeing block.

Furthermore, in the known tissue dyeing apparatus, the liquid discharge port and the cleaning liquid supply port are connected to a liquid discharge pipe and a cleaning liquid supply pipe at the lower surface of the dyeing block so that the dyeing block cannot be used for manual dyeing and cleaning operation.

SUMMARY OF THE INVENTION

An object of the present invention is to eliminate the above stated problems and to provide an apparatus for dyeing tissues in which the dyeing block or dyeing tray has a reduced bulk or can accommodate an increased number of slides for the same size and in which the dyeing tray can be accessed from above for supplying and sucking liquids so that the dyeing tray can be used also for manual dyeing operation.

According to the present invention, there is provided an apparatus for dyeing tissues comprising: a base; and dyeing trays provided on the base for supporting thereon slides each having a piece of tissue attached to an undersurface thereof; each of the dyeing trays comprising: a plateau having a flat top surface; drip surface means for receiving a liquid thereon, the drip surface means forming a continuation of the top surface adjacent to one end of the same; liquid discharge port means opening at the one end of the top surface of the plateau; liquid delivery port means opening in an upper surface of the dyeing tray and communicating with the liquid discharge port means through a passage in the dyeing tray, the liquid delivery port means being adapted to be connected to a suction source for discharging the liquid used on the plateau through the liquid discharge port means and the passage; bank means provided on the top surface of the plateau and extending from the one end of the top surface in a manner to form a partition between the drip surface means and the liquid discharge port means so as to prevent the liquid supplied on the drip surface means from flowing directly to the liquid discharge port means; and support means for supporting a slide above each plateau in such an attitude as to define a capillary gap between the top surface of the plateau and the undersurface of the slide.

The nature, utility, and further features of the present invention will be more clearly apparent from the following detailed description with respect to preferred embodiments of the invention when read in conjunction with the accompanying drawings.

DESCRIPTION OF THE PREFERRED EMBODIMENTS

Figure 1:
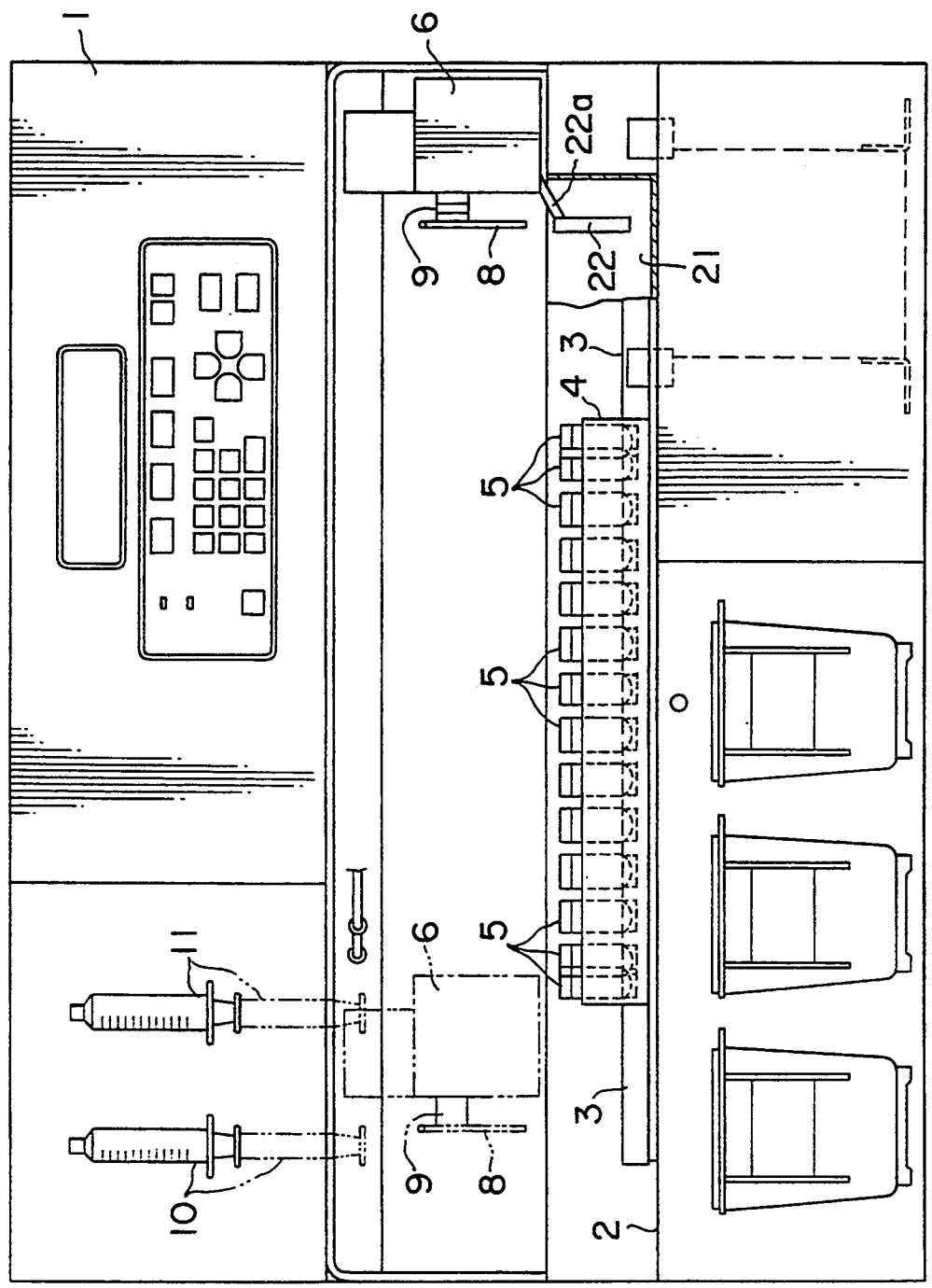
FIG. 1 is a front view of an apparatus for dyeing tissues in accordance with the present invention.
Figure 2:
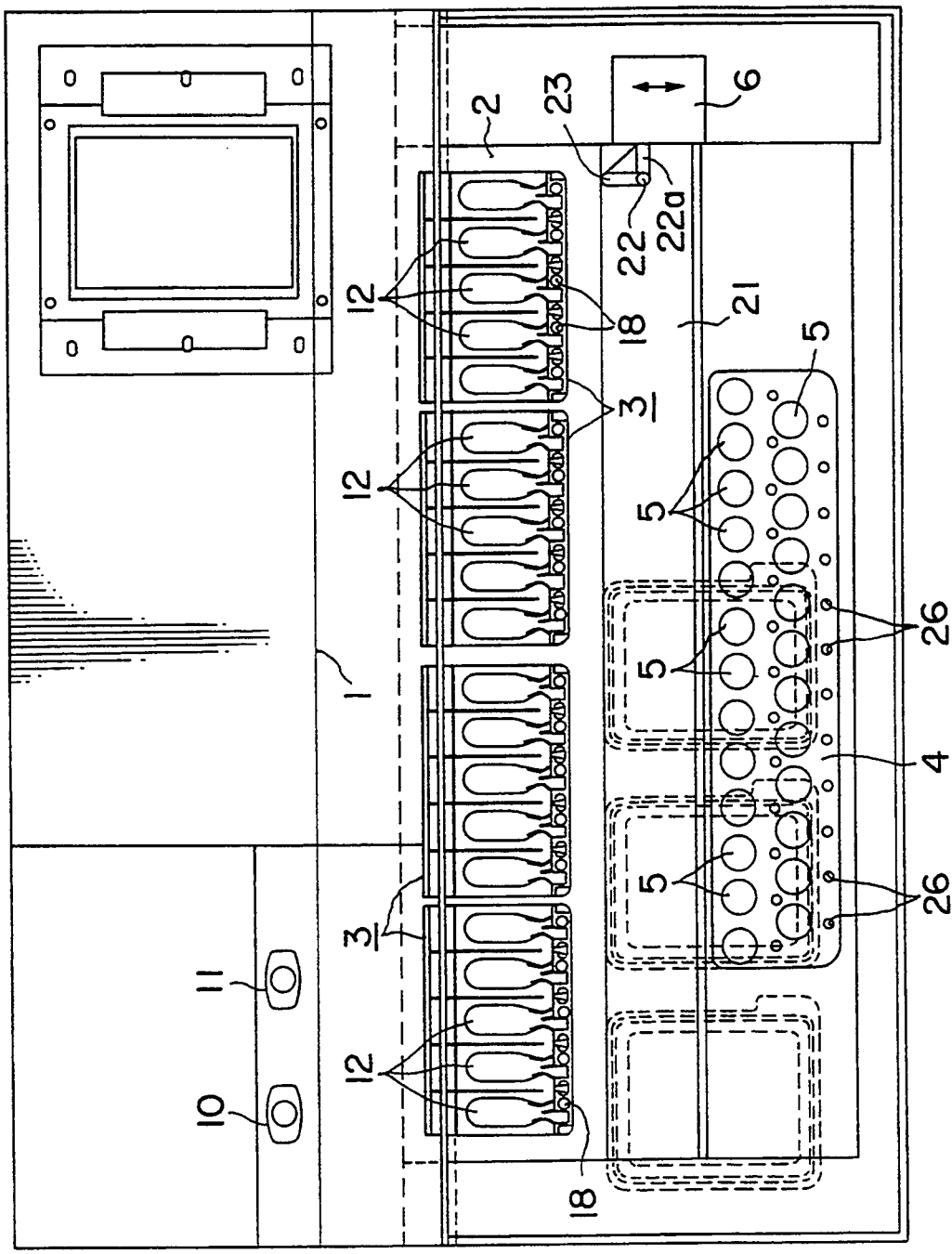
FIG. 2 is a top plan view thereof.
Figure 3:
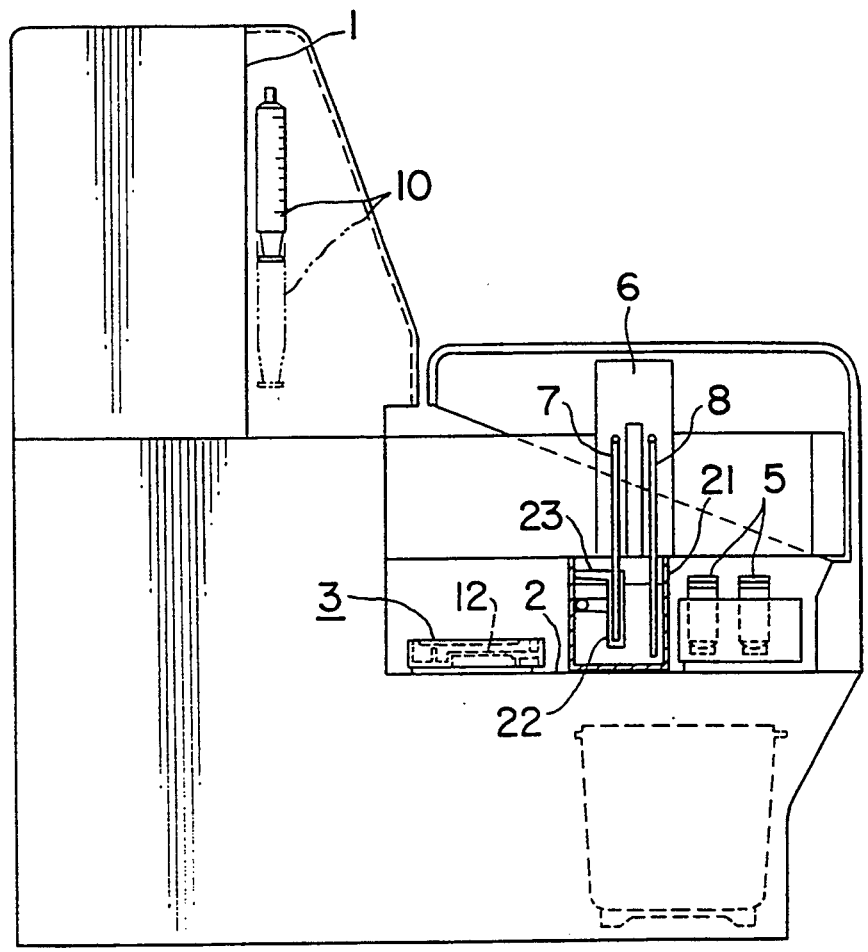
FIG. 3 is a side elevation thereof as viewed from the left in FIG. 2.

Referring first to FIGS. 1 through 3, there is generally shown an apparatus for dyeing tissues in accordance with the present invention. The dyeing apparatus has at its upper front a control panel 1. The control panel 1 includes at its front side a base 2 having a horizontal top surface. A plurality of dyeing trays 3 are arranged on the top surface of the base 2 in a predetermined direction or from the right to the left in FIG. 1 and 2. Parallel with the plurality of dyeing trays 3 is disposed a mounting board 4 which is also placed on the top surface of the base 2 and carries vertically thereon a plurality of dyeing liquid containers 5 each having an upper open end.

Figure 4:
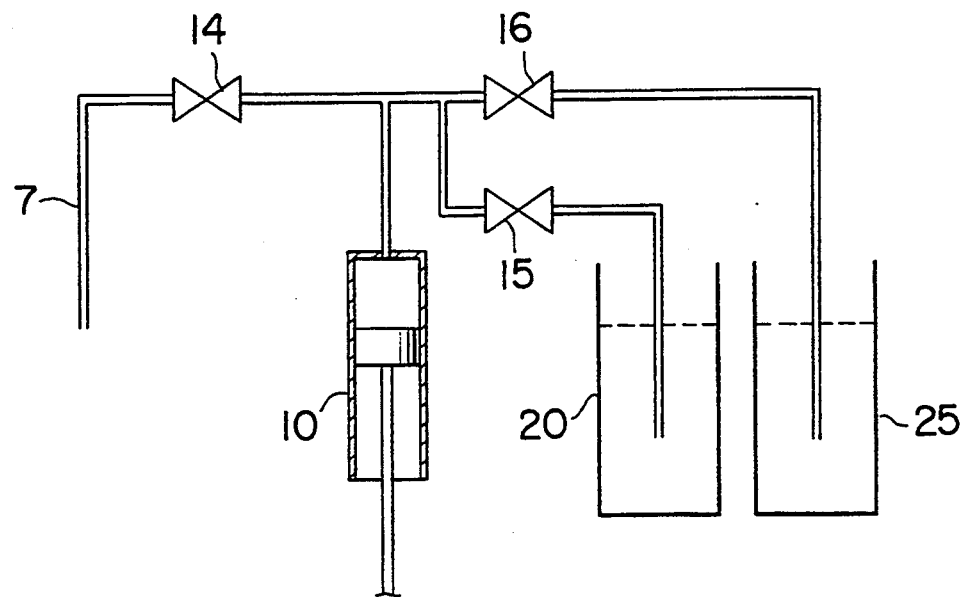
FIG. 4 is a piping diagram of a part supplying and discharging liquids through a drip tube in the apparatus for dyeing tissues.
Figure 5:
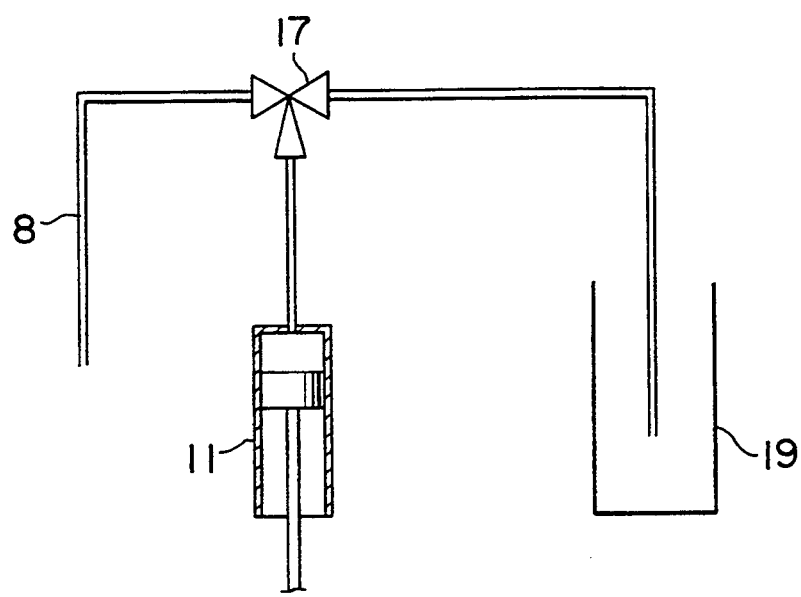
FIG. 5 is a piping diagram of a part discharging liquids through a suction tube in the same.

Furthermore, above the base 2 is an elongated carriage 6 provided displaceably in the above mentioned predetermined direction. The carriage 6 has on its one side (or on its left side in FIG. 2) a drip tube 7 and a suction tube 8 both provided displaceably vertically and in a direction along the longitudinal direction of the elongated carriage 6. The tubes 7 and 8 are both supported vertically on a single bracket 9 so as to be displaced in unison with each other. The drip tube 7 communicates with a first supply/discharge pumping cylinder 10 making use of a syringe via a piping as shown in FIG. 4, while the suction tube 8 communicates with a second supply/discharge pumping cylinder 11 utilizing a syringe by way of a piping as shown in FIG. 5.

When a dyeing operation is carried out, a plurality of (e.g., five in the embodiment shown) glass slides S are mounted on respective dyeing trays 3 in such a manner that a piece of tissue adhesively attached to each slide S confronts the upper surface of a plateau 12 (FIG. 2) centrally provided on each of the dyeing trays 3.

Figure 6:
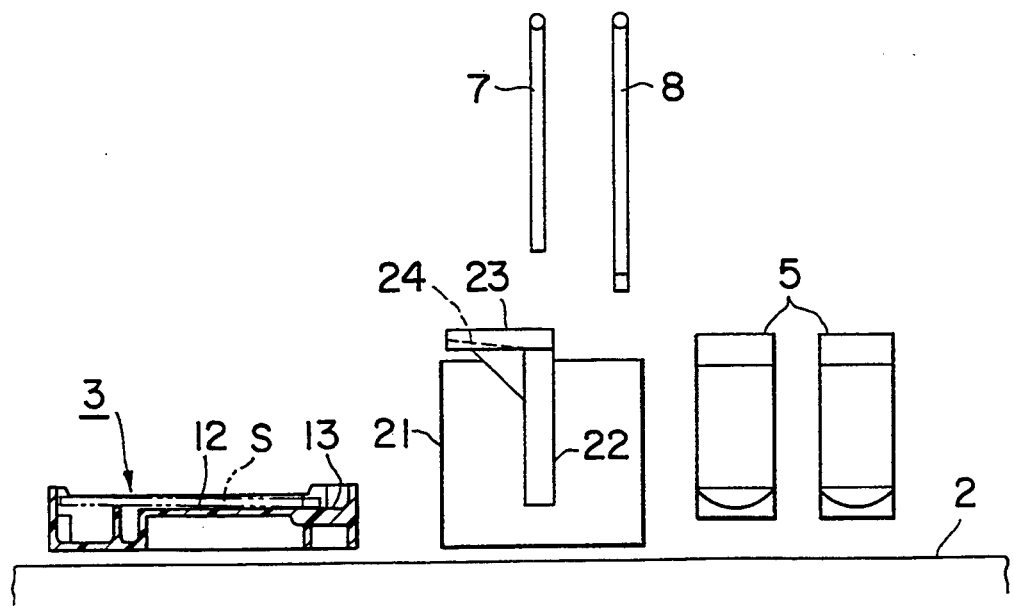
FIG. 6 is an enlarged schematic view corresponding to the part of FIG. 3 and showing the relationship among a dyeing tray, a liquid discharge tank, a rinsing container, the drip tube, the suction tube and so on used in the apparatus for dyeing tissues.
Figure 7:
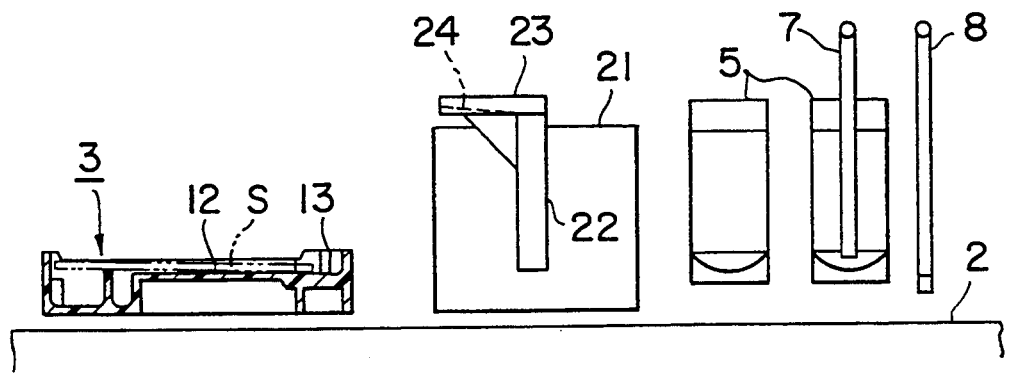
FIG. 7 is a view similar to FIG. 6 showing a state in which a dyeing liquid is being sucked into the drip tube.

The drip tube 7 and the suction tube 8 are then displaced from their neutral positions shown in FIG. 6 to positions shown in FIG. 7, and the drip tube 7 is inserted into any one of the dyeing liquid containers 5. Thereafter, among three solenoid valves 14 through 16 provided in the piping shown in FIG. 4, only the solenoid valve 14 provided between the drip tube 7 and the first supply/discharge pumping cylinder 10 is opened and the internal volume of the first pumping cylinder 10 is increased to thereby draw up a desired amount of dyeing liquid into the drip tube 7. At this time, the suction tube 8 is inserted into any one of a multiplicity of circular holes 26 (FIG. 2) formed in the mounting board 4.

Subsequently, the drip tube 7 and the suction tube 8 are again displaced. As is apparent from FIG. 8, the drip tube 7 is moved to a position immediately above any one of drip surfaces 13 which are provided on the top surfaces of the dyeing tray 3 continuously to the top surfaces of the corresponding plateaus 12, respectively. The first pumping cylinder 10 is then reduced in its volume to cause a small amount of dyeing liquid to drip onto the drip surface 13.

By virtue of capillarity, the dyeing liquid which has been dripped on the drip surface 13 is caused to permeate into a wedge-shaped gap C formed between the undersurface of the slide S placed on the dyeing tray 3 and the top surface of the plateau 12, and comes into contact with the piece of tissue attached to the undersurface of the slide S for the treatment thereof. After a predetermined duration of treatment, the bottom end of the suction tube 8 is abutted, as shown in FIG. 9, against a discharge port 18 formed in the top surface at the edge of the dyeing tray 3 so that the dyeing liquid within the gap is discharged through the discharge port 18.

Figure 9:
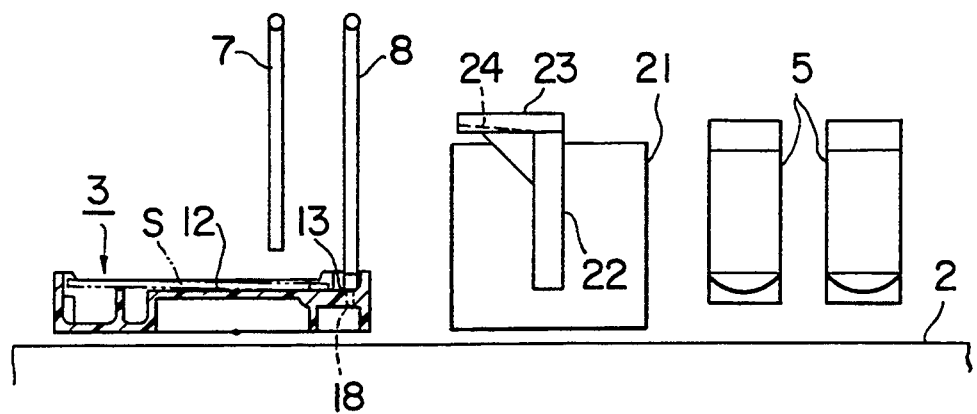
FIG. 9 is a view similar to FIG. 6 showing a state in which the liquid is being discharged from the dyeing tray.

More specifically, a three-way valve 17 (FIG. 5) is switched to a position permitting the suction tube 8 to communicate with the second pumping cylinder 11 while leaving the suction tube 8 in the state shown in FIG. 9, and the second pumping cylinder 11 is increased in its volume to thereby suck the dyeing liquid existing within the gap C into the second cylinder 11.

Figure 8:
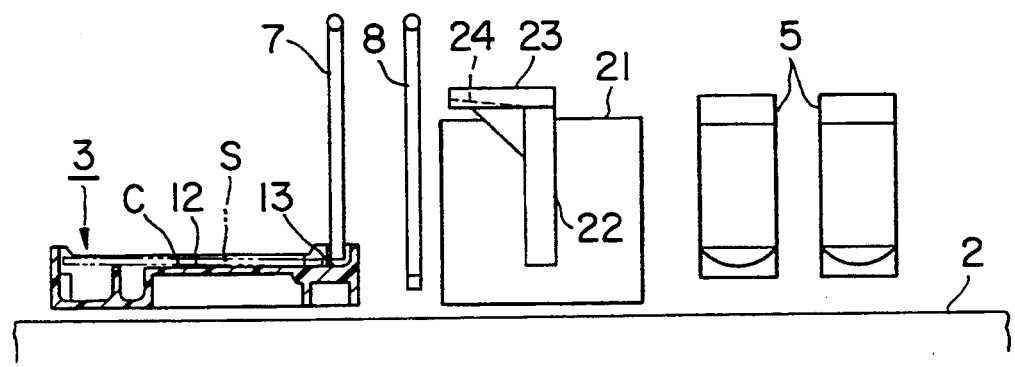
FIG. 8 is a view similar to FIG. 6 showing a state in which the dyeing liquid is being dripped onto the dyeing tray.

After the completion of the operation discharging the dyeing liquid from the gap C, the drip tube 7 and the suction tube 8 are returned to the position shown in FIG. 8, and a buffer solution is dripped onto the drip surface 13 through the drip tube 7 to fill the gap C with the buffer solution. At the time of dripping the buffer solution, only the solenoid valve 15 communicating into a buffer solution container 20 is opened among the three solenoid valve 14 through 16 shown in FIG. 4, and the volume of the first pumping cylinder 10 is increased so as to suck the buffer solution into the first pumping cylinder 10. Upon the completion of a desired amount of suction of the buffer solution, the solenoid valve 15 is closed while the solenoid valve 14 leading into the drip tube 7 is opened, and the volume of the first pumping cylinder 10 is reduced to cause the buffer solution to drip onto the drip surface 13.

The buffer solution thus dripped onto the drip surface 13 and filled into the gap C is discharged into a waste liquid bottle 19 by way of the suction tube 8. Thereafter, the gap C is filled with a different dyeing liquid by means of the drip tube 7. Afterward, the above-described procedure is repeated to dye the piece of tissue being attached to the underside of the slide and facing the top of the plateau 12 of each of the dyeing trays 3.

In the case of thus configured dyeing apparatus, however, the single drip tube 7 is used to drip plural kinds of the dyeing liquids and the buffer liquid, and hence different kinds of liquids must be prevented from mingling with one another. A careful attention is required for the dyeing liquids, in particular, since they are liable to cause deterioration due to the mixture of the different kinds. It is disadvantageously inevitable that a dyeing liquid adheres to the outer surface of the drip tube 7 when inserting the drip tube into the dyeing liquid container 5 in order to suck the dyeing liquid into the drip tube 7.

For this reason, a cleaning or rinsing tub may be provided at a corner of the base 2 so that the drip tube 7 can be moved into the rinsing tub for the cleaning thereof every time the dyeing liquid to be dripped is changed, which will adversely take an additional time for the movement of the drip tube 7 (and the suction tube 8). Thus the operation time required for dyeing is prolonged.

While on the contrary, the suction tube 8 need not be cleaned or rinsed whenever the dyeing liquid is changed. In order to prevent the inner passage of the suction tube 8 from being clogged up due to the crystallization of the buffer solution remaining inside, however, the interior thereof must be cleaned or rinsed after the completion of the dyeing operation. The following measures may be taken for the execution of this cleaning or rinsing.

As shown in FIGS. 2 and 3, the top surface of the base 2 of the dyeing apparatus includes an elongated discharge tank 21 having a rectangular configuration and extending from the right to the left in FIG. 2 throughout the region in which the elongated carriage 6 with the drip tube 7 and suction tube 8 is displaced.

Within the discharge tank 21 the elongated carriage 6 has a closed-end rinsing container 22 in cylindrical form extending vertically and fixedly supported thereon by way of a bracket 22a (FIG. 1). The rinsing container 22 has a bore of a size enough to receive the drip tube 7 and the suction tube 8 one by one. The rinsing container 22 further has on its upper side a gutter 23 secured thereto. The gutter 23 has a bottom surface 24 (FIG. 12) declining toward the rinsing container 22 so as to allow the liquid supplied onto the top surface to freely flow into the rinsing container 22. The positional relationship between the gutter 23 and the rinsing container 22 corresponds to that between the drip tube 7 and the suction tube 8. In other words, in case the drip tube 7 is located on the left of the suction tube 8 as indicated in FIGS. 6 through 11, the gutter 23 is placed on the left of the upper end of the rinsing container 22.

Furthermore, the lower end of the drip tube 7 is positioned slightly above the lower end of the suction tube 8 as shown in FIGS. 6 through 11, to thereby ensure that the drip tube 7 confronts the top surface of the extremity of the gutter 23 when the lower end of the suction tube 8 is inserted into the upper part of the rinsing container 22.

In addition, the piping leading to the drip tube 7 is connected to the first pumping cylinder 10 and via the solenoid valve 16 to a rinsing liquid container 25, thus constituting a rinsing liquid supply device for supplying the rinsing liquid through the drip tube 7 as illustrated in FIG. 4.

In the thus configured dyeing apparatus of the present invention, the cleaning or rinsing of the drip tube 7 and the suction tube 8 is executed as follows.

Figure 10:
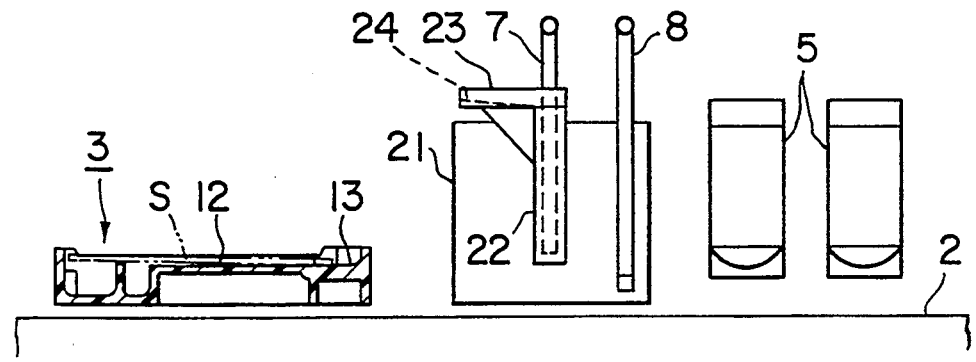
FIG. 10 is a view similar to FIG. 6 showing the drip tube being rinsed.

First, for rinsing the drip tube 7, the rinsing liquid supply system is activated with the drip tube 7 fully inserted into the rinsing container 22 as is clear from FIG. 10. In other words, only the solenoid valve 14 in FIG. 4 is opened and the volume of the first pumping cylinder 10 is increased to suck the rinsing liquid from the rinsing liquid container 25 into the first pumping cylinder 10. Subsequently, the solenoid valve 14 is opened with the solenoid valve 16 closed, and then the first pumping cylinder 10 is reduced in its volume. As a result, the rinsing liquid is ejected through the drip tube 7 into the rinsing container 22.

The rinsing liquid ejected through the drip tube 7 into the rinsing container 22 overflows the upper end opening of the container 22 and is discharged into the discharge tank 21. In this process, the rinsing liquid serves to clean not only the inner surface of the drip tube 7 but also the outer surface thereof. Therefore, the drip tube 7 extracted from the rinsing container 22 after the completion of the cleaning operation is substantially free from the dyeing liquid which has adhered thereto during the preceding dyeing liquid dripping operation, whereby different kinds of dyeing liquids are prevented from mingling with each other during the subsequent dyeing liquid dripping operation.

Since the rinsing container 22 and the gutter 23 are moved together with the dripping tube 7 and the suction tube 8 while being supported on the elongated carriage 6, the distance from both the tubes 7 and 8 to the rinsing container 22 and the gutter 23 is constantly short. Accordingly, the distance by which the tubes 7 and 8 are to be displaced for the rinsing of the tube 7 is shortened, which results in a time-saving rinsing operation.

Figure 11:
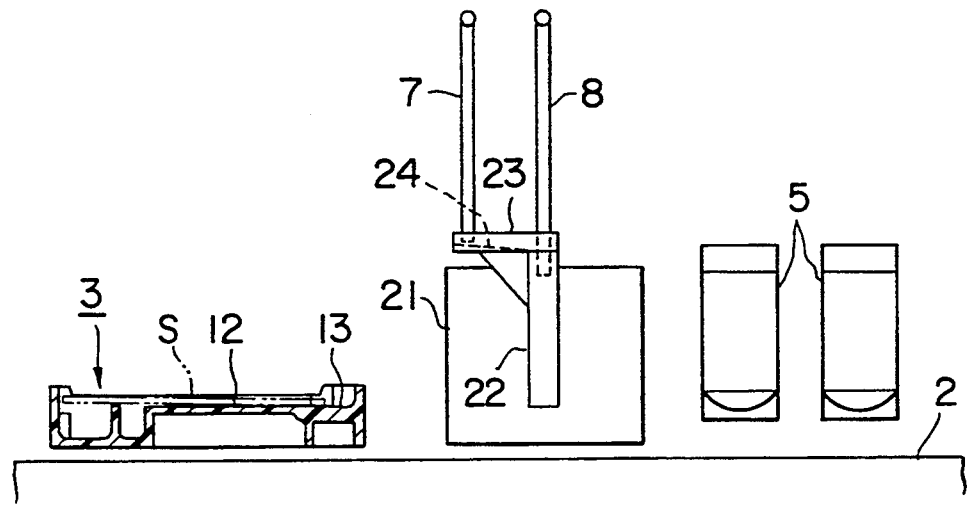
FIG. 11 is a view similar to FIG. 6 showing the suction tube being cleaned.

Second, when the interior of the suction tube 8 is to be cleaned for the purpose of washing off the buffer solution remaining within the suction tube 8 after the completion of the dyeing operation, the lower end of the suction tube 8 is inserted into the upper part of the rinsing container 22 while causing the dripping tube 7 to confront the top surface at the extremity of the gutter 23 as shown in FIG. 11.

In this state, the three solenoid valves 14 through 16 and the first pumping cylinder 10 as shown in FIG. 4 are actuated in the same manner as the rinsing operation for the drip tube 7 described above, to thereby eject the rinsing liquid through the drip tube 7 into the gutter 23. At the same time, the three-way valve 17 shown in FIG. 5 is changed to a position permitting the suction tube 8 to communicate with the second pumping cylinder 11, and the volume of the second pumping cylinder 11 is increased.

As a result, the rinsing liquid is supplied into the rinsing container 22 while being sucked by the suction tube 8, whereby the buffer solution remaining within the suction tube 8 is sucked up together with the rinsing liquid into the second pumping cylinder 11. After the completion of the rinsing operation, the rinsing liquid sucked into the second pumping cylinder 11 and containing the buffer solution is discharged into a waste liquid bottle 19 by virtue of the above-described changeover of the three-way valve 17 and the reduction in volume of the second pumping cylinder 11.

In order to securely prevent different liquids from being mingled with each other, a distilled water may be previously introduced into the drip tube 7 at the time of drawing up a liquid into the drip tube 7. The lower end of the distilled water is brought into a location slightly above the lower end of the drip tube 7 previous to the insertion of the drip tube 7 into the dyeing liquid container 5. Accordingly, bubbles will intervene between the liquid and the distilled water when sucking the liquid into the drip tube 7, which eliminates the possibility of the dilution of the liquid by the distilled water.

In the case where the liquid is dripped onto the drip surface 13 of the dyeing tray 3, the volume of the bubbles are utilized to permit only the drip of the liquid and prohibit the drip of the distilled water onto the drip surface 13. After the drip of the liquid onto the drip surface 13, the drip tube 7 is shifted above the discharge tank 21 to eject the distilled water through the drip tube 7, thus effecting a pre-cleaning of the interior of the drip tube 7.

Figure 12:
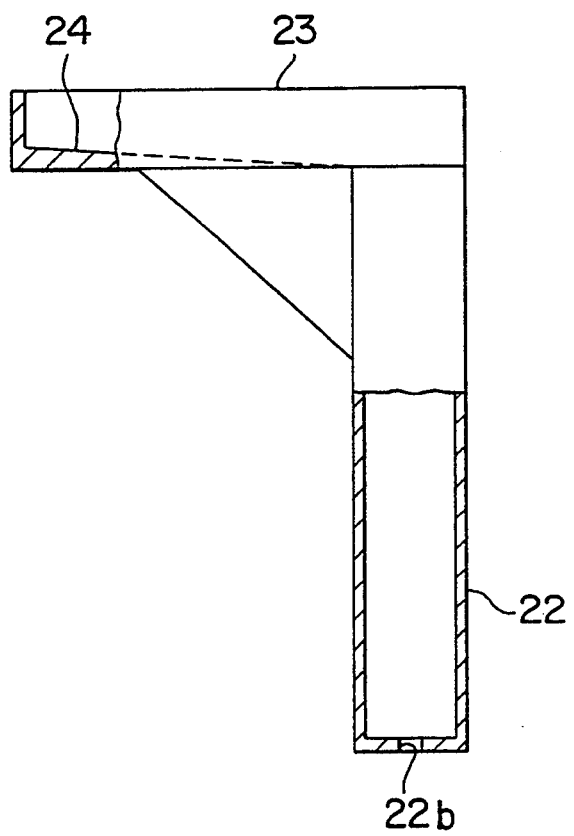
FIG. 12 is an enlarged view, partly in section, of the rinsing container and a gutter.

Moreover, in order to prevent the mixture between liquids which may arise from the dyeing liquid diluted by the rinsing liquid and remaining inside the rinsing container 22, a through-hole 22b may be provided in the bottom of the rinsing container 22 as shown in FIG. 12 and the first pumping cylinder 10 may be designed to be able to force via the drip tube 7 into the rinsing container 22 an amount of the rinsing liquid exceeding the amount to be discharged through the through-hole 22b.

This construction prevents a dyeing liquid diluted by the rinsing liquid from remaining inside the rinsing container 22, and eliminates any possibility that the dyeing liquid are undesirably mingled with each other.

As described above, the mixture of the dyeing liquids and the clogging of the tube with the buffer solution can thus be effectively prevented, ensuring a satisfactorily stable, short-time dyeing operation.

Figure 13:
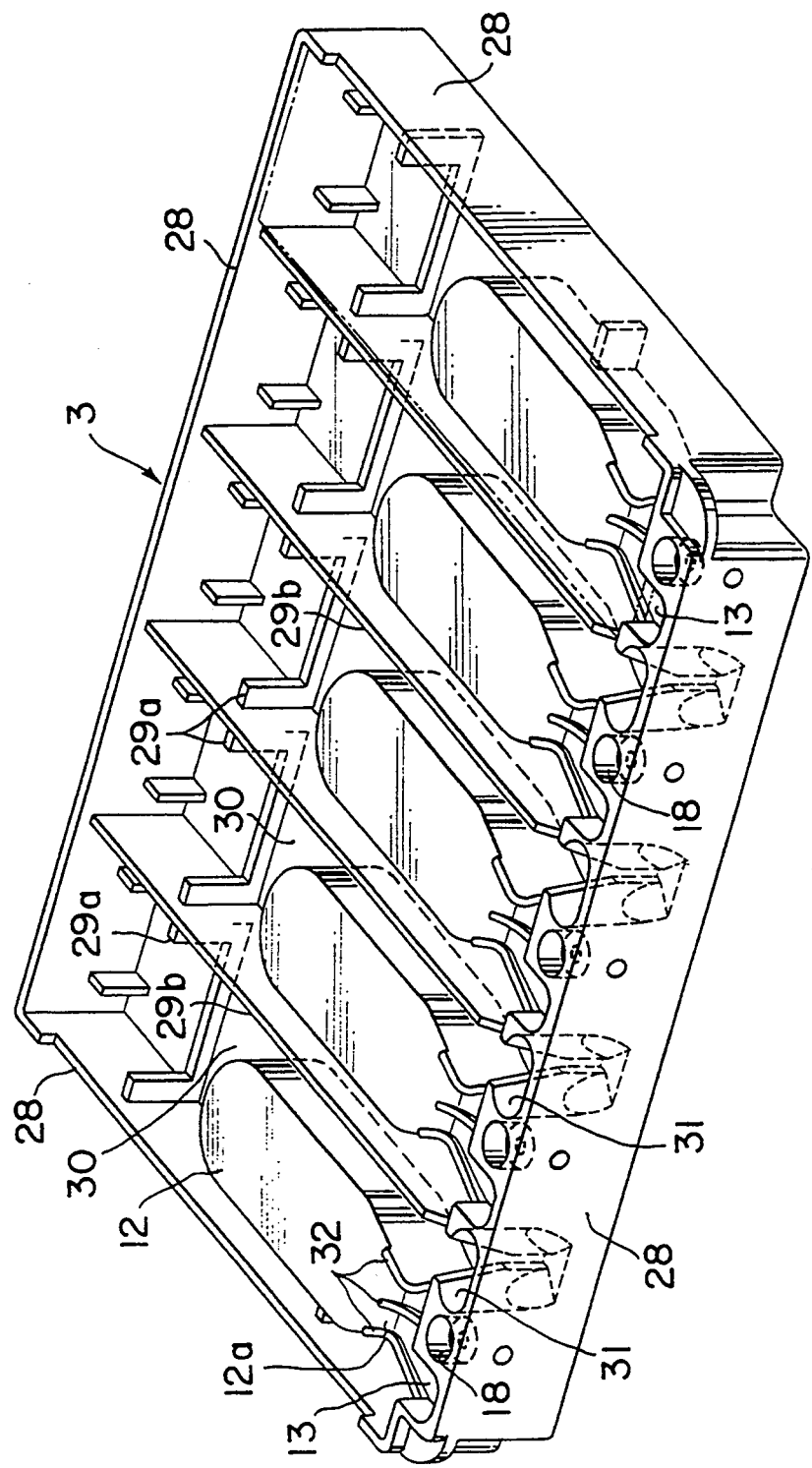
FIG. 13 is a perspective view showing details of the dyeing tray.
Figure 14:
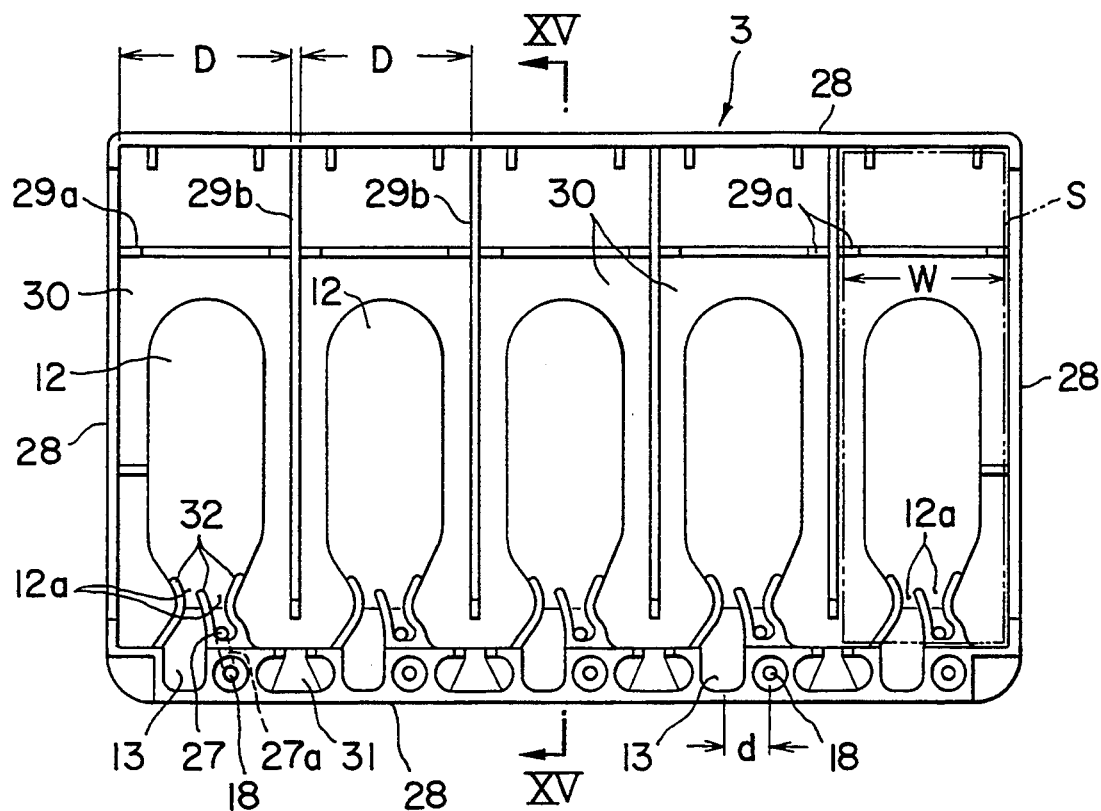
FIG. 14 is a top plan view thereof.
Figure 15:
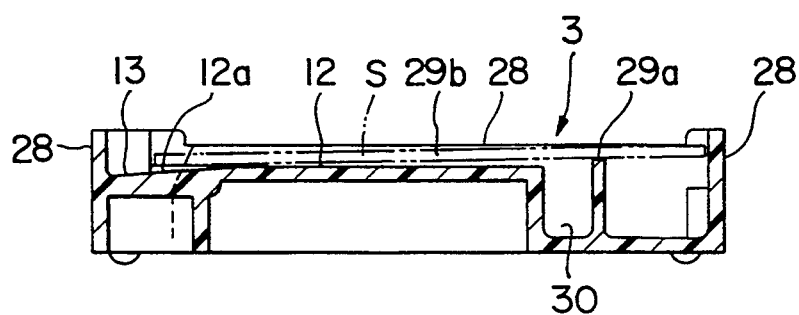
FIG. 15 is a sectional view taken along a line XV—XV in FIG. 14.

FIGS. 13 through 15 illustrate details of the dyeing tray 3. The dyeing tray 3 is integrally formed from fiber reinforced plastic or the like, and has a generally rectangular periphery surrounded by a wall 28. Inside the wall 28, there are provided a plurality of (e.g., five in the embodiment shown) plateaus 12 each facing a specimen of tissue attached to the underside of a glass slide S.

The drip surfaces 13 are each provided on one end (the lower end in FIG. 14) side of the corresponding plateaus 12, continuously to the corresponding top surfaces of the plateaus 12. The top surfaces of the plateaus 12 have regions 12a at one end (lower end as viewed in FIG. 14) thereof, respectively. These regions 12a are slightly declined or inclined to be lower toward the associated drip surfaces 13. On the other end side of the plateaus 12 are correspondingly provided support walls 29a spaced apart from the plateaus 12. It should be noted that the top edges of the support walls 29a are slightly higher than the top surfaces of the plateaus 12 as is apparent from FIG. 15.

In the surface regions 12a of the plateaus 12 there are provided liquid discharge ports 27 on one side (right side in FIG. 14) thereof, respectively. The regions 12a do not decline toward the discharge ports 27. Banks 32 having a small height extend along both edges of the surface regions 12a and between the discharge port 27 and the drip surface 13. The top edges of the banks 32 are formed at substantially the same level as the major top surfaces of the plateaus 12.

Furthermore, in the top surface of a part of the wall 28 which is located along one side (lower side in FIG. 14) of the dyeing tray 3, there are provided liquid delivery ports 18 arranged at intervals d with respect to the corresponding drip surfaces 13. Each delivery port 18 opens into one of the discharge ports 27 by way of a passage 27a (FIG. 14) formed within the dyeing tray 3.

In the embodiment shown there are upright walls 29b interposed between adjacent plateaus 12, with intervals D between adjacent upright walls 29b (FIG. 14). The interval D is slightly larger than the width W (FIG. 14) of the slides to which a tissue to be dyed is attached.

In addition, in the top surface of the part of the wall 28 provided with the drip surfaces 13 and the delivery ports 18, there are formed liquid supply recesses 31 opening into reservoirs 30 surrounding the plateaus 12, respectively, for voluntarily permitting the reservoirs 30 to be filled with an anti-drying liquid.

Figure 16:
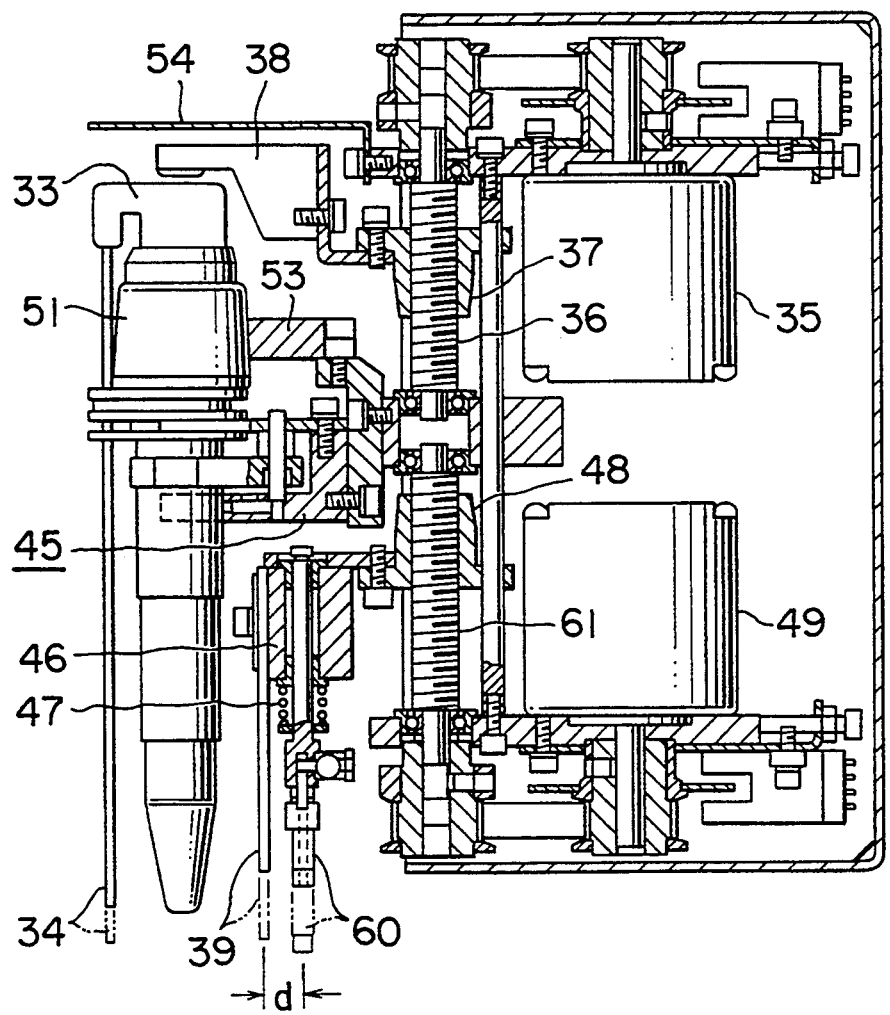
FIG. 16 is a longitudinal front view of a drip device.

Alternatively, the drip device for dripping a dyeing liquid onto the drip surface 13 provided on the top surface of the dyeing tray 3 configured as described above may comprise a dyeing liquid container 51 filled with a dyeing liquid, as shown in FIG. 16, and a dyeing liquid container grasping arm 45. The arm 45 acts as carrying means for carrying the dyeing liquid container 51 to a position above a predetermined dyeing tray 3 for the drip of the dyeing solution.

The dyeing liquid container 51 is designed to eject a dyeing solution being stored therein through an ejection tube 34 by depressing a push button 33 provided on the top portion of the container 51. For free depression of the push button 33, the base end of a pressing member 38-is secured to a first nut 37 screwed with a first threaded rod 36 which is rotated by a first motor 35, while the tip of the pressing member 38 is located to face the top surface of the push button 33.

Figure 17:
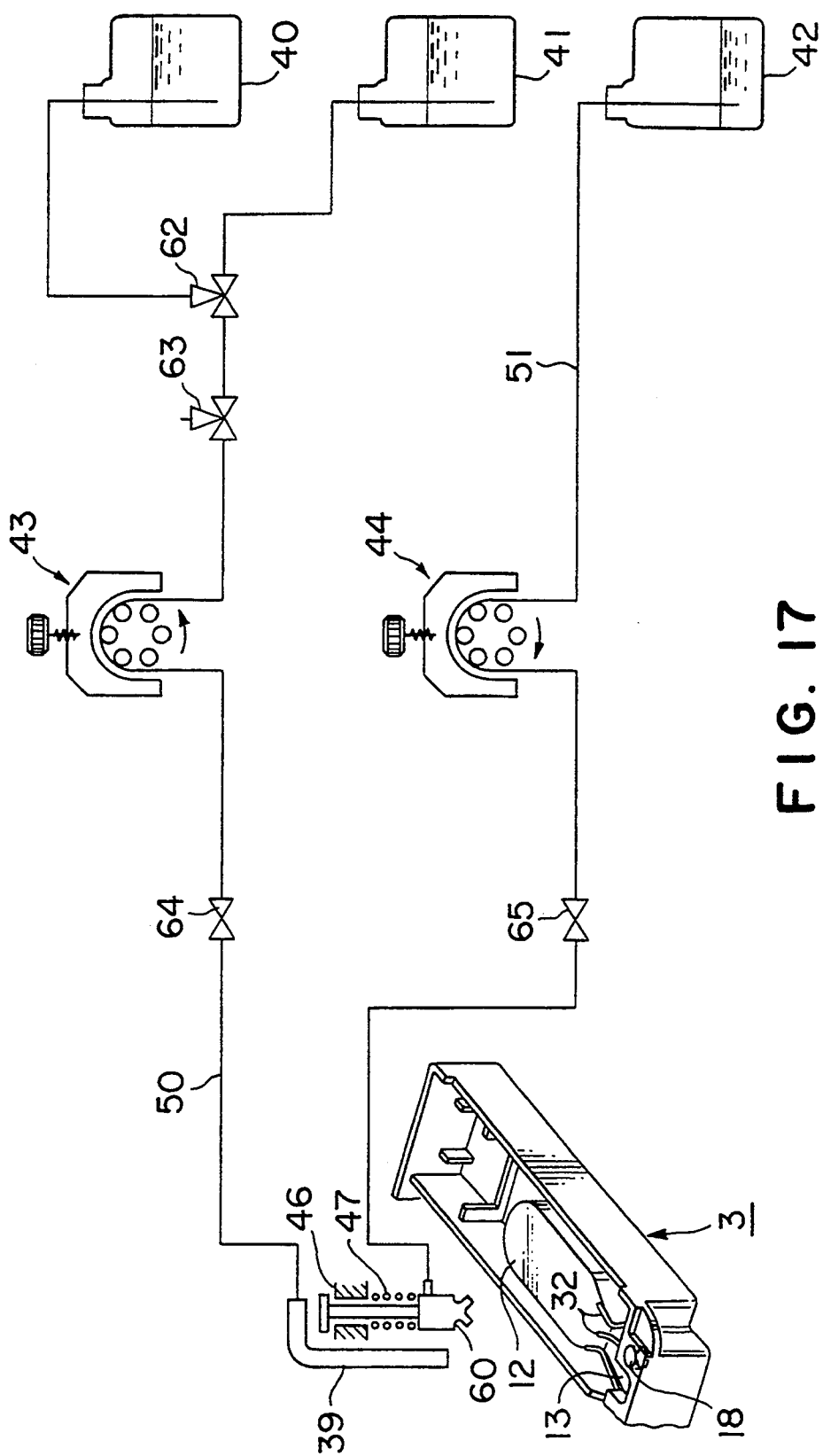
FIG. 17 is a circuit diagram of a rinsing system.

The rinsing device for washing off the dyeing liquid forced between the top surfaces of the plateaus 12 and the undersurfaces of the slides S includes a liquid supply tube 39 and a liquid discharge tube 60 as shown in FIGS. 16 and 17. The liquid supply tube 39 is connectable to a rinsing liquid container 40 or a distilled water container 41 serving as a liquid supply means by way of a valve 64, a liquid supply pump 43 a valve 63 and a changeover valve 62, while the liquid discharge tube 60 is connected to a drain container 42 serving as a liquid discharge means through a liquid discharge pump 44.

The lower end opening of the liquid supply tube 39 is spaced apart from that of the liquid discharge tube 60 at an interval of d (FIG. 15) equal to the interval d (FIG. 14) between the drip surfaces 13 and the associated delivery ports 18 provided on the top surface at one end of the dyeing tray 3.

More specifically, the liquid supply tube 39 and the liquid discharge tube 60 are supported on a vertically movable bracket 46 in such a manner that they are allowed to be slightly displaced vertically. In particular, the liquid discharge tube 60 is biased downward under the influence of resiliency of a compression spring 47. A second nut 48 fixed to the rising bracket 46 is screwed with a second threaded rod 61 which is rotatable forwardly and reversely by means of a second motor 49. The bracket 46 is thus vertically displaced by the second motor 49. The assembly shown in FIG. 1 is mounted on a carriage (not shown) movable horizontally.

The upper end of the liquid supply tube 39 communicates with the rinsing liquid container 40 by way of a liquid supply tube 50 having the liquid supply pump 43 as shown in FIG. 17, so that the rinsing liquid can be dripped onto the drip surface 13 through the operation of the liquid supply pump 43. On the other hand, the upper end of the liquid discharge tube 60 communicates with the drain container 42 by way of the liquid discharge tube 51 equipped with the liquid discharge pump 44.

The dyeing liquid container grasping arm 45 has a sensor 53 for detecting whether or not the arm 45 grasps the dyeing liquid container 21. Furthermore, over the pressing member 38 is a push plate 54 extending horizontally and adapted to push a door open when introducing the dyeing liquid container grasping arm 45 into a dyeing liquid container housing 70 (FIG. 18).

Figure 18:
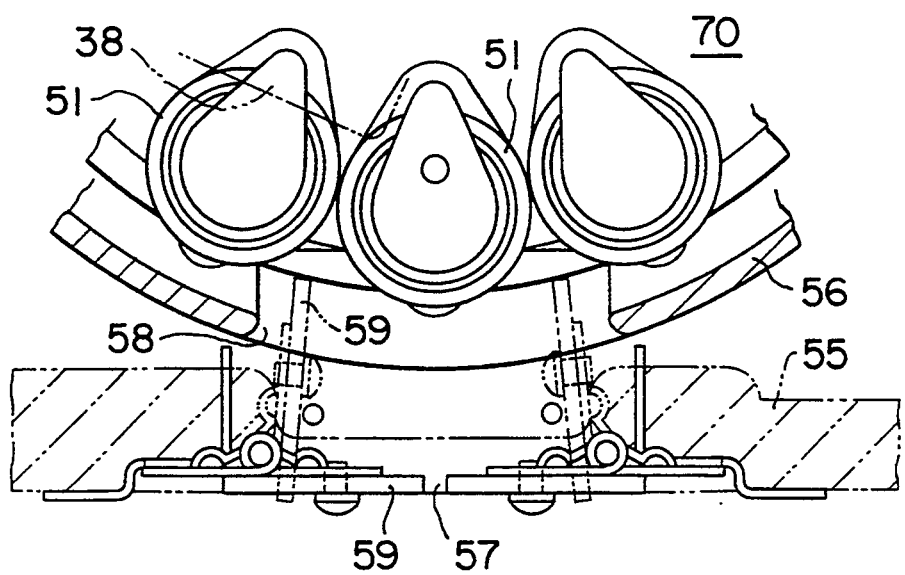
FIG. 18 is a partially cross-sectional view of a dyeing liquid container housing.

Due to the necessity of storing the dyeing liquids to be used in the dyeing operation at a lower temperature, the dyeing liquid container housing 70 is surrounded by an insulating wall 55, and a cooling wall 56 is provided around a turntable circumferentially holding a plurality of dyeing liquid containers 51 as shown in FIG. 18. When the dyeing liquid container grasping arm 45 is engaged with or disengaged from the dyeing liquid container 51, the arm 45 is introduced into the inside of the cooling wall 56 through openings 57 and 58 provided in the insulating wall 55 and the cooling wall 56, respectively. The opening 57 in the insulating wall 55 is provided with a pair of oppositely openable doors 59 which are resiliently forced to be closed by a spring.

The push plate 54 serves to push the doors 59 with a horizontal movement of the dyeing liquid container grasping arm 54 to turn the doors 59 from a closed position shown by solid lines in FIG. 18 to an open position shown by broken lines.

By the use of the thus configured dyeing apparatus of the present invention, the dyeing treatment for tissues attached to the slides is carried out as follows.

In order to support the slides whose undersurfaces have tissues attached thereto above the corresponding plateaus 12, respectively, the undersurfaces at one end of the slides are put on the top surfaces at one end (lower end in FIG. 14) of the plateaus 12 while the undersurfaces adjacent to the other end are put on the top edge of the support wall 29a as designated by chain lines in FIG. 14.

Under such conditions, the drip surfaces 13 formed on the top surfaces at the one end of the plateaus 12 are exposed beyond one edges of the associated slides S because the drip surfaces 13 extend into the wall 28, and wedge-shaped capillary gaps increasing in thickness from the drip surfaces 13 toward the support walls 29a are correspondingly defined between the top surfaces of the plateaus 12 and the undersurfaces of the slides S. The side edges of the slides S are in close proximity to the inner side edges of the wall 28 extending along the sides of the dyeing tray 3 and to the side edges of the upright walls 29b interposed between adjacent plateaus 12.

With the slides S positioned as described above, the dyeing liquid is dripped onto the drip surfaces 13 formed on the plateaus 12 at one end thereof by using the dyeing liquid container 51 acting as a drip means. Then, the dyeing liquid is caused to permeate through the wedge-shaped gaps defined between the undersurface of the slides and the top surfaces of the plateaus by virtue of capillarity, consequently dyeing the tissues attached to the undersurfaces of the slides and facing the corresponding gap.

At this time, rapid evaporation of the dyeing liquid introduced into the gaps can be prevented because of the close proximity of the side edges of the slides S relative to the sides of the upright walls 29b (or inner sides of the wall 28). If there is a need for more securely preventing the dyeing liquid from evaporation, distilled water or the like may be introduced into the reservoir 30 surrounding the plateaus through the liquid supply recesses 31.

For the execution of the dripping operation of the dyeing liquid, the first threaded rod 36 is rotated by the first motor 35 to depress the push button 33 of the dyeing liquid container 51 by way of the first nut 37 and the pressing member 38 for the ejection of the dyeing liquid through the ejection tube 34.

It is to be appreciated that previous to the ejecting operation the dyeing liquid container grasping arm 45 takes out a predetermined dyeing liquid container 51 from within the dyeing liquid container housing 70, and moves the ejection tube 34 attached to the dyeing liquid container 51 to a position above the drip surface 13 of the predetermined dyeing tray 3.

After the completion of the dyeing operation for a predetermined period of time by the use of the dyeing liquid, the dyeing liquid is discharged. Subsequently, the rinsing liquid is supplied by the rinsing system to wash off the dyeing liquid adhering to the inside of the gap. Prior to the wash-off rinsing treatment, the lower end of the liquid supply tube 39 making up the rinsing system is moved to a position above the drip surface 13 while the lower end of the liquid discharge tube 60 is connected to the liquid delivery port 18.

By means of a drive mechanism as that of the elongated carriage shown in FIG. 1, the liquid supply tube 39 and the liquid discharge tube 60 making up the rinsing system shown in FIGS. 16 and 17 are moved to positions directly above a selected drip surface 13 and a corresponding liquid discharge port 18, and then the second threaded rod 61 is rotated by the second motor 49 to lower the bracket 46 which has moved upward so far, thereby positioning the liquid supply tube 39 to immediately above the drip surface 13 and pressing the liquid discharge tube 60 against the selected liquid delivery port 18.

The liquid discharge tube 60 is allowed to vertically displace relative to the bracket 46, and is urged downward by the resiliency of the compression spring 47. Furthermore, the lower end opening of the discharge tube 60 has a periphery sealed with a sealing material such as a rubber ring. Hence, the press of the liquid discharge tube 60 against the liquid delivery port 18 with the descending motion of the bracket 46 provides a liquid-tight connection between the lower end of the liquid discharge tube 60 making up the rinsing system and the liquid delivery port 18.

For the execution of the rinsing treatment, the rinsing liquid stored within the rinsing liquid container 40 is forced into the gaps defined between the top surfaces of the plateaus 12 and the undersurfaces of the slides S through the liquid supply tube 39 and the drip surfaces 13, by actuating the liquid supply pump 43 provided in the liquid supply tube 50.

After lapse of a predetermined period of time, posterior to the introduction of the rinsing liquid into the gaps, the liquid discharge pump 44 provided in the liquid discharge tube 51 leading into the drain container 42 is activated to discharge the rinsing liquid through the liquid discharge port 18 and the liquid discharge tube 60. The rinsing operation is thus effected.

In the embodiment shown, the bank 32 is formed not only between each drip surface 13 onto which the dyeing or cleaning liquid is dripped and each discharge port 27, but also on both side edges of the region leading to the drip surface 13 and the discharge port 27, whereby the dyeing or cleaning liquid which has been dripped onto the drip surface 13 is prevented from flowing directly into the discharge ports 27. Furthermore, the banks 32 on both side edges serve to direct the liquid on the drip surface 13 to the major surface of the plateau 12, and to direct the used liquid on the major surface to the discharge port 27. As a result, the dyeing liquid is brought into intimate contact with the tissues attached to the undersurface of the slides, and moreover a satisfactory removal of the dyeing liquid by rinsing is ensured.

Subsequent to a predetermined rinsing operation, the dyeing liquid is again dripped onto the drip surfaces 13 provided on the plateaus 12 by using the dyeing liquid container 51, and is caused to permeate through the gaps defined between the top surfaces of the plateaus 12 and the undersurfaces of the slides S for executing the dyeing treatment of the tissues attached to the undersurfaces of the slides.

Afterward, the above-described operation is repeated a predetermined number of times to obtain a desired dyeing treatment.

The interior of the liquid supply tube 39 and liquid discharge tube 60 is properly washed with distilled water so as to prevent the rinsing liquid from drying and crystallizing within the tubes 39 and 60, which would otherwise bring about clogging of the tubes.

At the time of completion of the operation, a three-way valve 62 shown in FIG. 17 is changed over, with the lower ends of the liquid supply tube 39 and the liquid discharge tube 60 positioned as shown in FIGS. 10 and 11, thereby allowing the liquid supply tube 50 to communicate with the distilled water container 41 and actuating the liquid supply pump 43 as well as the liquid discharge pump 44.

As a result, the interior of each member of the rinsing system including the liquid supply tube 39 and the liquid discharge tube 60 can be properly cleaned. At this time, in order to facilitate the rinsing operation, air may be introduced into the distilled water through a suction valve if necessary. In FIG. 17, reference numerals 64 and 65 denote solenoid-actuated valves which are opened in unison with the energization of the liquid supply pump 43 and the liquid discharge pump 44, and are closed in unison with the deenergization thereof.

It should be noted in this case that a syringe or pipette is used to feed the dyeing liquid or rinsing liquid onto the drip surface 13 and to remove the dyeing liquid from the delivery port 18.

In that case, the dyeing tray 3 can be covered with a lid such as a transparent resin plate to obtain a sufficient moisture retention, thereby securely preventing the tissues from drying irrespective of a long-period dyeing operation. Furthermore, the dyeing trays may be stacked up so as to reduce the working area required for a multiplicity of dyeing operation.

The dyeing apparatus of the present invention is thus configured and functions, and hence a dyeing treatment of specimens such as tissues for the observation of immunoreaction, for example, can be executed with a small amount of the dyeing liquid, which greatly contributes to the reduction of cost and labor required for the dyeing treatment for purposes such as the observation of immunoreaction. More advantageously, there is no need to force out the air at the start of the dyeing operation, which leads to not only simplification of the preliminary process for the dyeing operation but also the curtailment of the cost for manufacturing the apparatus because of unnecessary complicated piping system provided with a rotary change-over valve.

More conveniently, the dyeing tray is not only loaded into the dyeing apparatus to perform an automatic dying operation, but also applicable to a variety of manual dyeing operations, and accordingly the instrument management can be simplified in laboratories or the like in which a multiplicity of dyeing operations are carried out.

What is claimed is:

1. Apparatus for dyeing tissues comprising:
   a base; and
   a dyeing tray provided on the base for supporting thereon slides each having a piece of tissue attached to an undersurface thereof, said dyeing tray comprising;
   a plateau having a flat top surface;
   drip surface means for receiving a liquid thereon, said drip surface means being located adjacent to an end of said top surface and being lower than the top surface, said top surface having a declining region which is adjacent to the drip surface means and which gradually declines toward the drip surface means;
   liquid discharge port means opening at said end of the top surface of the plateau and adapted to be connected to a suction source for discharging the liquid used on said plateau through the liquid discharge port;
   a first bank provided on said top surface of the plateau and extending along said declining region of the top surface so as to form a partition between said declining region and said liquid discharge port means so as to prevent the liquid supplied on the drip surface means from flowing directly to said liquid discharge port means;
   two second banks provided along two side edges of the plateau in regions adjacent to said first bank such that said declining region is located between said first bank and one of said second banks and said liquid discharge port means is disposed between said first bank and the other of said second banks; and
   support means for supporting a slide above said plateau in such an attitude as to define a capillary gap between the top surface of the plateau and the undersurface of the slide, said support means being configured to position the slide so that the slide covers said plateau and said declining region but does not cover said drip surface means.

2. The apparatus according to claim 1, further comprising:
   liquid delivery port means opening in an upper surface of the dyeing tray and communicating with said liquid discharge port means through a passage in the dyeing tray, said liquid delivery port means being adapted to be connected to said suction source.

3. The apparatus according to claim 1, further comprising:
   wall means provided on said dyeing tray so as to surround said plateau, said wall means being configured to define a space surrounded thereby and having such a shape and a size as to receive said slide therein with edges of the slide closely adjacent to the wall means, whereby rapid evaporation of the liquid in the tray is prevented.

4. The apparatus according to claim 1, wherein said plateau is reduced in transverse width in an area thereof having said first and second banks.

5. The apparatus according to claim 1, wherein all of said banks have a height substantially equal to the height of the top surface of the plateau.

6. The apparatus according to claim 1, wherein said support means comprises said banks and support wall means erected in the vicinity of another end of the plateau.

7. The apparatus according to claim 1, wherein said dyeing tray further comprises a liquid reservoir surrounding the plateau, and liquid supply recess means provided in the tray for communication with the reservoir.

8. The apparatus according to claim 2, further comprising:

liquid dripping means for dripping a dyeing liquid;

carriage means for displacing the liquid dripping means to and away from a position above said drip surface means; and rinsing means including a liquid supply tube and a liquid discharge tube disposed with a distance therebetween which is equal to a distance between said drip surface means and said liquid delivery port means, said liquid supply tube and said liquid discharge tube being movable so that the lower opening of the liquid supply tube will be directly above said drip surface means and said liquid discharge tube will be connected to said liquid delivery port, said rinsing means further including liquid supply means connected to said liquid supply tube, and liquid discharge means connected to said liquid discharge tube.

9. The apparatus according to claim 1, further comprising:

a plurality of dyeing liquid containers supported on said base alongside said dyeing tray;

a carriage movable horizontally above said base;

a drip tube and a suction-tube supported on said carriage so as to be displaceable horizontally therealong as well as vertically;

a liquid discharge tank provided in said base in a region within which said carriage is moved horizontally;

a rinsing container with a bottom, supported by said carriage above said liquid discharge tank so as to allow insertion of said drip tube or said suction tube into the rinsing container, selectively;

a gutter fixed to a side of the upper end of said rinsing container for causing a rinsing liquid supplied onto the gutter to flow into the rinsing container;

rinsing liquid supply means connected to said drip tube to cause the rinsing liquid to drip through the drip tube; and said gutter extending from said rinsing container by a horizontal distance which is equal to the horizontal distance between the drip tube and the suction tube, said drip tube having a lower open end located at a higher level than a lower open end of said suction tube, whereby when the lower open end of the suction tube is inserted into the rinsing container the lower open end of the drip tube will be opposed to an end of the gutter.

10. The apparatus according to claim 9, wherein the bottom of said rinsing container has a through hole therein.

11. The apparatus according to claim 9, further comprising means for supplying the rinsing liquid or a buffer solution selectively through the drip tube.

* * * * *